Figure 1:
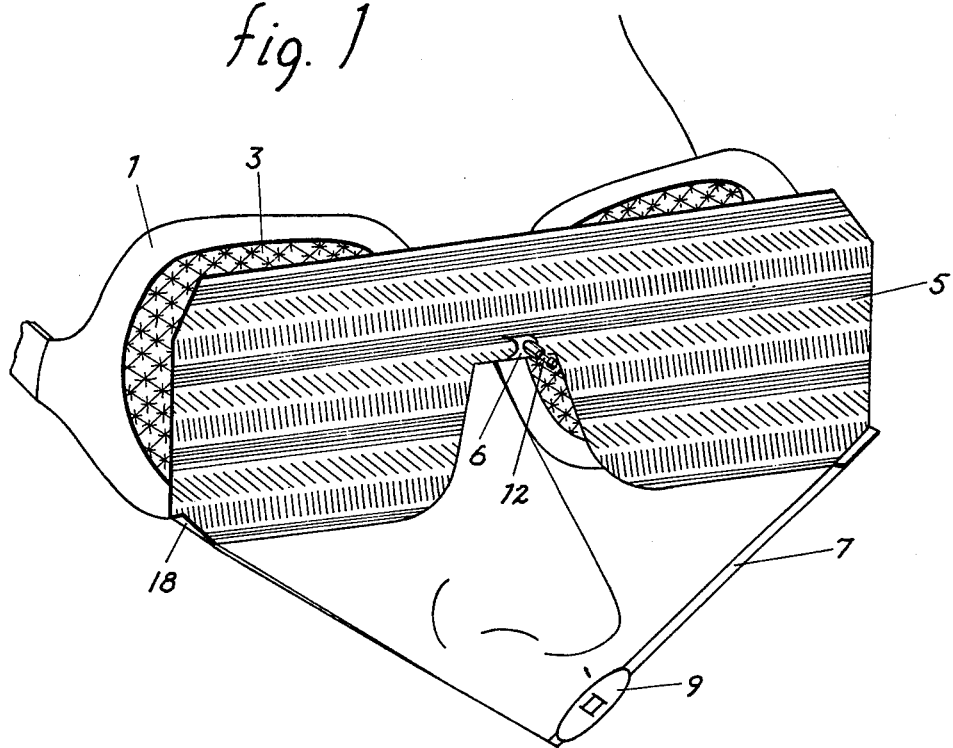

United States Patent
Dehlinger

[11] 3,972,319
[45] Aug. 3, 1976

[54] WIND MOSAIC GLASSES

[76] Inventor: Peter Jean Dehlinger, 4219 SW. Condor Ave., Portland, Oreg. 97201

[22] Filed: Jan. 26, 1976

[21] Appl. No.: 652,479

[52] U.S. Cl. .............................. 128/1 C; 128/76.5; 351/44
[51] Int. Cl.² ....................................... A61M 21/00
[58] Field of Search ............... 128/1 C, 76.5; 351/44

[56] References Cited
UNITED STATES PATENTS

| | | | |
|---|---|---|---|
| 1,515,389 | 11/1924 | Hopkins | 351/44 |
| 3,470,870 | 10/1969 | Schoffer | 128/1 C |

FOREIGN PATENTS OR APPLICATIONS

| | | | |
|---|---|---|---|
| 27,889 | 11/1909 | United Kingdom | 128/1 C |

*Primary Examiner*—Dalton L. Truluck

[57] ABSTRACT

Novelty glasses by which the wearer can visualize the rate and evenness of his breathing. The glasses comprise a conventional eyeglasses frame which supports a pair of multifaceted lenses in the lens support positions of the frame. Rotatably attached to the frame is a lightweight projection plate bearing a light-transmissive pattern. The plane of rotation of the projection plate is substantially parallel to the plane of the lenses, and the lateral distance between the plate and the lenses is easily adjusted. A stiff nose strap attached to the projection plate extends in an arc which passes under the wearer's nose when the lateral position of the projection plate is properly adjusted. The strap supports a slidably attached nose sail which can be positioned at any point along the strap to optimally intercept the nose-exhaled breath of the wearer. In this configuration, the wearer's nose-exhaled breath pushes the sail outwardly, causing the attached projection plate to rotate slightly away from its angular equilibration position, whereby the wearer observes a moving mosaic pattern.

4 Claims, 2 Drawing Figures

U.S. Patent   Aug. 3, 1976   3,972,319

WIND MOSAIC GLASSES

The present invention relates to image projectors; in particular, to image projectors in which the object to be projected is moved by currents of air.

The applicant's prior U.S. patent application for Meditation Viewer, Ser. No. 624,382, filed on Oct. 21, 1975, discloses a type of novelty glasses by which the wearer can visualize the rate and evenness of his breathing. The Meditation Viewer invention was designed for use in achieving a meditational or otherwise relaxed state, based on the finding that relaxation can be induced by concentrating on one's breathing rhythm. The principle feature of the earlier described invention is the coupling of the wearer's nose-exhaled breath to the rotational motion of a pair of projection discs positioned in the wearer's field of vision. This coupling is accomplished by a pair of nose sails, each of which extends from one of the discs to a position under the wearer's nose. As the wearer nose exhales, the force of the exhaled air pushes each sail outwardly, causing the discs to rotate slightly away from their equilibrium positions. This motion generates a moving pattern as seen by the wearer.

One of the problems associated with the Meditation Viewer glasses is that the rotational motion of the projection discs derives from the force of air exhaled from each nostril separately. As a consequence, if one of the wearer's nostrils is partially or completely blocked, as is not uncommon with many people, only one of the two projection discs will be breath-activated, and the moving pattern will be seen in one eye only. A further limitation of the earlier disclosed glasses is that the position of the nose sails relative to the frame is fixed according to the shape of the wires which hold the nose sails to the discs. Repositioning the sails in order to optimize the response of the sails to the nose exhaled breath requires reshaping these wires, a difficult task at best.

The present invention in Wind Mosaic Glasses is designed to overcome the two limitations of the Meditation Viewer mentioned above. The invention comprises a conventional eyeglasses frame bearing a pair of multifaceted lenses, similar to the earlier disclosed invention. The present invention differs from the earlier one in that the wearer's nose-exhaled breath is coupled to a single projection plate rather than a pair of projection discs. The projection plate is rotatably mounted on a pin which projects outwardly from the nose bridge of the frame, such that the plane of plate rotation is substantially parallel to the plane of the lenses. The distance between the plate and the lenses is easily adjusted by means of a friction fitting adjustment member on the pin. A stiff nose strap attached to the projection plate passes directly underneath the wearer's nose when the lateral position of the plate is properly adjusted. This strap supports a slidably attached nose sail which can be positioned at any point along the strap to optimally intercept the nose-exhaled breath of the wearer. In this configuration the wearer's nose-exhaled breath forces the sail outwardly, causing the attached projection plate to rotate slightly away from its equilibrium position, whereby the wearer ses a mosaic pattern which moves simultaneously before both eyes.

Accordingly, it is an object of the present invention to provide a simple, durable, and effective type of novelty glasses by which the wearer can visualize the rate and evenness of his breathing.

It is another object of this invention to provide a device which is worn like a pair of conventional eyeglasses, and which couples the nose-exhaled breath of the wearer, issuing from a single nostril, to the rotational movement of a single projection plate overlaping the visual field of both of the wearer's eyes.

It is another object of the invention to provide means for easily adjusting the breath-intercepting element of the glasses to optimally intercept the wearer's nose-exhaled breath.

It is yet another object of the invention to provide a type of novelty glasses which is relaxing in its effect and at the same time, visually rewarding to the wearer.

These and other objects and features of the invention will now be described by reference to the figures, in which: FIG. 1 is a perspective view of the glasses, showing the relevant facial features of the wearer; and FIG. 2 is a top view of the glasses.

Referring to FIG. 1, the invention comprises a conventional spectacles frame 1; a pair of multifaceted lenses 3 which are held in the lens positions of the frame; a projection plate 5 which is rotatably attached to the frame; and a stiff nose strap 7 attached to the two sides of the projection plate and extending in an arc below the wearer's nose, where a slidably attached nose sail 9 serves to intercept the wearer's nose-exhaled breath.

Figure 2:
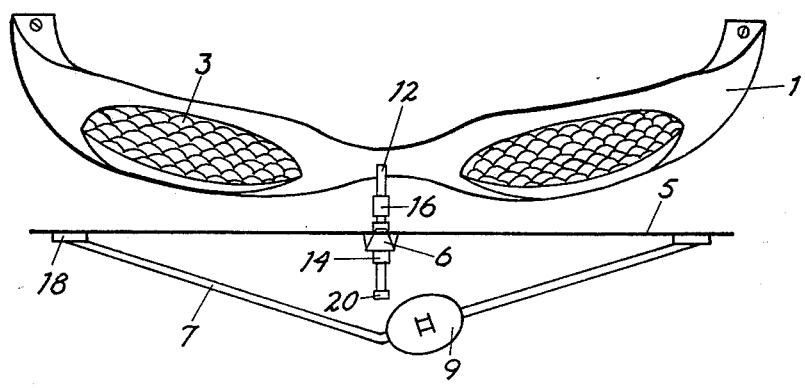

In the first embodiment to be described, shown in FIGS. 1 and 2, the multifaceted lenses are translucent plates with an embossed mosaic surface on one side. The mosaic surface consists of a rectangular array of small inverted pyramids, which serves to refract incoming light in several directions. The projection plate is a stiff plastic sheet material, such as printer's screen tint, and bears a transparent color pattern, for example a tightly grouped set of red, green, and blue parallel lines, as shown in FIG. 1. Illumination is provided by an external light, either sunlight or an artificial indoor light. The illuminating light passes through the projection plate and the resultant color pattern is then mutliply refracted by the mosaic screens. The wearer thus sees a variegated color pattern.

In a second embodiment, the glasses are adapted so that the wearer sees a moire' pattern, as described in the prior application for Meditation Viewer. In a third embodiment, the lenses are made opaque except for a small area near the center of each lens, where a multifaceted transparent object such as a rhinestone is attached to the lens. The projection plate bears a transparent color pattern and is preferably embossed in the regions which overlap the two multifaceted lens objects.

Securely attached to the nose bridge of the frame and projecting perpendicularly outward therefrom is a stiff metal pin 12. The projection plate is attached to the pin for rotation about the axis of the pin. The mode of attachment of the projection plate to the pin is by way of a polyethylene sleeve 14 which rotates freely on the pin. The sleeve is attached to the projection plate through two holes, one located along the upper midline of te plate and the other located in the center of an upwardly bent plate tab 6, the end of which tab is inserted into a plate slit directly above the first described hole. With the sleeve inserted through these holes and positioned perpendicular to the plane of the plate, the sleeve and the tab end are permanently bonded to the plate. The plate sleeve is slipped over the pin and the plate is subsequently secured to the pin by pin cap 20.

The lateral distance between the projection plate and the mosaic lenses is set by the position of the plate adjustment member 16 which is attached to the pin by friction fit, proximal to the plate sleeve. During normal use of the glasses, when the wearer is in a relaxed sitting or reclining position, the pin 12 will point upward and the plate will gravitationally assume the lateral position where the plate sleeve contacts the plate adjustment member. In the present embodiment the distance between the plate and the lenses can be vaired from about 2 centimeters to 4 centimeters.

A stiff lightweight strap 7 is attached to the color-projecting plate at the two lower corners of the plate. The tips 18 of these corners are bent outwardly 90° and the ends of the strap bonded to corner tips such that the strap makes a downwardly extending arc or shallow V, the plane of which intersects the plate at an angle of about 20°. Slidably attached to the nose strap is an ovalshaped nose sail 9 having two parallel slits through which the strap interfits. The nose sail can be easily positioned on the strap by manually moving the sail along the strap. The strap and sail are preferably constructed from light-weight stiff plastic sheet material, such as polyvinyl or polycarbonate sheet.

The overall operation of the glasses can now be appreciated by reference to FIG. 1. During normal use, in which the wearer is in a relaxed sitting or reclining position, head forward, the projection plate comes to rest at an angular equilibrium position where the plate is roughly symetrical with the frame. The wearer adjusts the lateral position of the plate by changing the position of the plate adjustment member on the pin until the nose strap intersects the region of greatest nose-exhaled force under the nose. The wearer then moves the nose sail under the nostril providing the greater nose-exhaled force. It will be appreciated that in practice the nose sail can be positioned at any point along the strap, depending on the degree of breath-driven plate motion desired. In this configuration, the wearer's nose-exhaled breath engages the nose sail and moves it outwardly, causing the attached projection plate to rotate slightly away from its equilibrium position. The wearer then observes a moving pattern. As the wearer completes his exhalation and begins to inhale, the plate resumes its angular equilibrium position and the moving pattern completes one oscillation in response to one breathing cycle.

I claim:

1. Novelty glasses by which the wearer can visualize the rate and evenness of his breathing, comprising:
   a. a frame;
   b. a projection plate rotatably attached to the frame, said plate overlapping the visual field of both of the wearer's eyes;
   c. a shape-retaining nose strap attached to said plate; and
   d. a nose sail held by the nose strap in such position that the nose sail intercepts the nose-exhaled breath of the wearer, causing the attached projection plate to rotate slightly away from its equilibrium position.

2. The glasses of claim 1 including means for adjusting the lateral position of the projection plate relative to the frame.

3. The glasses of claim 1 in which the nose sail is moveable along said nose strap, such that the nose sail can be positioned under either of the wearer's nostrils.

4. Novelty glasses to be worn like a pair of conventional eyeglasses by which the wearer can visualize the rate and evenness of his breathing, comprising:
   a. a conventional eyeglasses frame supporting a pair of lenses in the two lens positions of the frame;
   b. a pin attached to the frame, said pin extending outwardly in a direction substantially perpendicular to the plane of the lenses;
   c. a lightweight projection plate bearing a light-transmissive pattern on its surface, said plate being rotatably mounted on said pin;
   d. means for adjusting the lateral position of said plate on said pin;
   e. a shape-retaining nose strap attached to said plate and extending underneath the wearer's nose when the lateral position of said plate properly adjusted; and
   f. a nose sail slidably attached to the nose strap such that the nose sail can be positioned under either of the wearer's nostrils.

* * * * *